(12) United States Patent
Hunt et al.

(10) Patent No.: US 7,523,042 B2
(45) Date of Patent: Apr. 21, 2009

(54) PROCESS AND SYSTEM FOR ENHANCING MEDICAL PATIENT CARE

(75) Inventors: Jacquelyn Suzanne Hunt, North Plains, OR (US); Joseph Siemienczuk, Clackamas, OR (US)

(73) Assignee: Providence Medical Group, a division of Providence Health System - Oregon, Portland, OR (US)

( * ) Notice: Subject to any disclaimer, the term of this patent is extended or adjusted under 35 U.S.C. 154(b) by 820 days.

(21) Appl. No.: 10/346,937

(22) Filed: Jan. 17, 2003

(65) Prior Publication Data

US 2004/0143462 A1    Jul. 22, 2004

(51) Int. Cl.
| | |
|---|---|
| *G06Q 10/00* | (2006.01) |
| *G06Q 50/00* | (2006.01) |
| *G06Q 40/00* | (2006.01) |
| *G06F 11/34* | (2006.01) |
| *H04M 3/51* | (2006.01) |

(52) U.S. Cl. .................. 705/2; 705/4; 705/11
(58) Field of Classification Search .............. 705/2, 705/3, 4, 11; 707/100
See application file for complete search history.

(56) References Cited

U.S. PATENT DOCUMENTS

| | | | | |
|---|---|---|---|---|
| 6,024,699 | A * | 2/2000 | Surwit et al. ............... | 600/300 |
| 6,151,581 | A * | 11/2000 | Kraftson et al. ............ | 705/3 |
| 6,363,393 | B1 * | 3/2002 | Ribitzky ..................... | 707/102 |
| 6,381,484 | B1 * | 4/2002 | Ayanruoh ................... | 600/407 |
| 6,381,576 | B1 * | 4/2002 | Gilbert ....................... | 705/2 |
| 6,383,136 | B1 * | 5/2002 | Jordan ........................ | 600/300 |
| 6,401,072 | B1 * | 6/2002 | Haudenschild et al. ...... | 705/3 |
| 2002/0011250 | A1 * | 1/2002 | Stewart et al. ............. | 128/898 |
| 2002/0038227 | A1 * | 3/2002 | Fey et al. .................... | 705/3 |
| 2002/0052761 | A1 * | 5/2002 | Fey et al. .................... | 705/2 |
| 2002/0072933 | A1 * | 6/2002 | Vonk et al. .................. | 705/2 |

* cited by examiner

*Primary Examiner*—C Luke Gilligan
*Assistant Examiner*—Amber L Altschul
(74) *Attorney, Agent, or Firm*—Alleman Hall McCoy Russell & Tuttle LLP

(57) ABSTRACT

A process and/or system that extracts selected information from e.g. traditional electronics medical records to enable analysis of a determined medical condition shared by multiple patients. A data warehouse receives the extracted information and reformats that information to enable rapid analysis by a health care provider of that provider's patient population having that medical condition. It further collects the selective data of the selected patients for multiple health care providers and enables comparisons of health care providers' success for such patients to promote upgrading of the treatment by less successful providers.

8 Claims, 10 Drawing Sheets

FIG. 3

| Patient Name/# | Demographics | Problems | Medications | Allergies | Directives | Laboratory |
|---|---|---|---|---|---|---|
| Smith, John A. 658544-2 | DOB, age, gender, address, SS#, Insurance, Contacts | 414.41<br>428.0<br>427.31<br>401.1<br>433.10 | Warfarin<br>Furosemide<br>Metolazone<br>Metoprolol<br>Epoetin | Ampicillin<br>nuts | DNR | BP SYS 120<br>BP DIA 80<br>HDL 45<br>LDL 20<br>WT 198 |
| Rogers, David L. 647322-1 | DOB, age, gender, address, SS#, Insurance, Contacts | 427.31<br>424.0<br>272.0<br>477.9<br>722.52 | Digoxin<br>Pravastatin<br>Warfarin | NKA | No transf | WT 240<br>FLU 05 mg L<br>CHOLEST 285<br>BP SYS 125<br>BP DIA 90 |
| Johnson, Mary J. 533975-2 | DOB, age, gender, address, SS#, Insurance, Contacts | 747.10<br>746.9<br>286.5<br>272.0<br>493.00 | Warfarin<br>Amoxicillin<br>Atorvastatin | Iodine<br>Codeine | No decision | PULSE 50<br>RATE regular<br>TRIGLYC 240<br>FX father posi<br>WT 179 |
| Davis, Thomas C. 298225-2 | DOB, age, gender, address, SS#, Insurance, Contacts | 427.32<br>427.61<br>272.0<br>530.11<br>574.20 | Warfarin<br>Metoprolor<br>Diltiazem<br>Atorvastatin<br>Asprin | Bee venom<br>Latex | No code | BP SYS 110<br>BP DIA 80<br>PULSE 40<br>ENT wnl<br>SMOK HX 10y |
| Parker, Susan M. 488700-1 | DOB, age, gender, address, SS#, Insurance, Contacts | 394.9<br>414.01<br>428.0<br>427.31<br>401.1 | Warfarin<br>Spironolacton<br>Furosemide<br>Digoxin<br>Nitroglycerin | Sulfa | DNR | WT 135<br>INR 3.0<br>GLUCOSE 120<br>BMD – 2.0 |

Provider: Marcus Welby, MD

RISK FACTORS FOR HEART DISEASE

| Patient name | DOB | Age | Gender | Cholesterol | HTN | DM | 10-Year Risk Score |
|---|---|---|---|---|---|---|---|
| Smith, John A. | 4/12/1935 | 67 | M | 180 | YES | YES | 17% |
| Rogers, David L. | 9/27/1920 | 82 | M | 130 | NO | NO | 17% |
| Johnson, Mary J. | 2/17/1915 | 87 | F | 150 | YES | NO | 17% |

FIG. 5

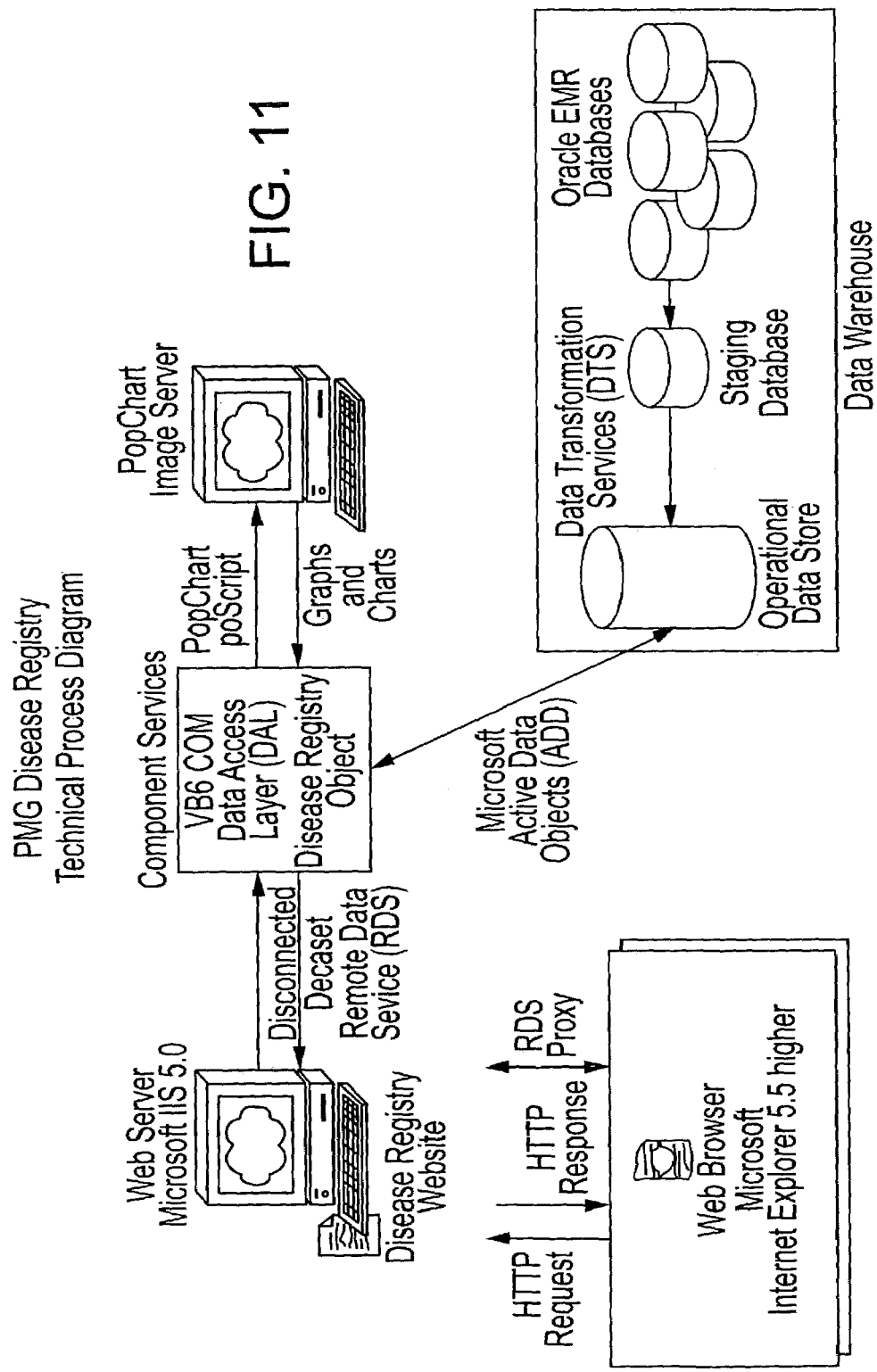

PROCESS AND SYSTEM FOR ENHANCING MEDICAL PATIENT CARE

FIELD OF THE INVENTION

This invention relates to a process and system that enables health care providers to access pertinent information that has been queried from available electronic medical record database(s) and other electronic data sources, and more particularly to a process and system that is automatically reformatted to facilitate efficient and higher quality medical decision-making.

BACKGROUND OF THE INVENTION

In 2001 the Institute of Medicine (IOM) published the findings of its extensive research on the American healthcare system. In summary, the IOM found that healthcare in America frequently falls short in its ability to translate knowledge into practice and to apply new technology. A central deficiency contributing to this momentous problem is characterized as "episodic care" (e.g., care is limited to patient initiated visits to health care providers) and is compounded by lack of readily available information technology for enabling optimum care processes.

In the predominant model of healthcare delivery in America, patients only receive care if and when they attend an appointment with a healthcare provider. This model has become increasingly problematic as American healthcare has shifted its focus from acute care to the management of chronic conditions. Chronic conditions are now the leading cause of illness, disability, and death. They affect almost half of the US population and account for the majority of healthcare expenses. In caring for chronic conditions there exists the imperative to track patients and pertinent aspects of their care. Unlike acute diseases (e.g., heart attack, pneumonia), chronic diseases (e.g., hypertension, diabetes) are typically asymptomatic for long periods of time, often decades. As a result patients do not have the same impetus to proactively seek medical care. Unfortunately, this neglect of medical care often leads to irreversible consequences (e.g., stroke, blindness, death).

Although information technology in the way of electronic medical records and point-of-care electronic alerts are finding their way into healthcare, these systems do not allow a healthcare provider to easily track and monitor patients in a chronic care model. No electronic system exists to bring patients and needed care to the attention of the healthcare provider in the absence of patient-initiated contact. Historically, a variety of paper-based methods have been employed to track patients and care processes. These methods are inefficient and do not capitalize on information technology. Where electronic patient tracking methods have been employed, the systems have generally not been directed at the level of the healthcare provider and require manual entry of data.

The state of existing methods for patient and care process tracking is exemplified by warfarin, an anticoagulant or "blood thinner," most typically prescribed to prevent stroke. Warfarin is considered a high-risk medication because underdosing can result in a higher risk of stroke and over-dosing can result in hemorrhage. As a result of these risks, close monitoring of monthly blood tests is recommended to assure appropriate individualized dosing. Methods for tracking dose and frequency of the needed blood tests range from reliance on patient memory to card filing systems. Electronic tracking systems are stand-alone and do not capitalize on existing information sources, therefore requiring manual data entry of pertinent patient information. In the case where electronic data exists, on-demand queries can produce simple reports, however this is an inefficient method of data tracking.

Although care of chronic diseases is enhanced by tracking of patients and their healthcare data, the improvements in care are not as robust as when healthcare providers are exposed to their individual performance rates. Most chronic disease states have one or more measurable indicators that reflect provider performance and correlate with patient outcomes. National guidelines and published papers provide clear guidance on the choice of measurable indicators. Published evidence supports the hypothesis that feedback of a healthcare provider's performance data, benchmarked against peers' data, promotes better outcomes. The sources of currently available performance data are administrative, primarily billing claims data. Since the primary use for this data is financial, it is often inaccurate and not inclusive of the data elements necessary to characterize patient outcomes and provider performance. Additionally, based on the time cycle of claims acquisition, the feedback of this data is delayed four to eighteen months.

Continuing medical education is a prerequisite for desirable patient health outcomes, but is insufficient in and of itself. When educational forums are provided to healthcare providers, research shows that uptake and retention of information is minimal. However, it is known that when this education is teamed with improved systems of care and/or feedback of performance, care to the patient is significantly improved.

SUMMARY OF THE INVENTION

The present invention extracts relevant information from an electronic medical record (EMR) database, which can be supplemented by other electronic sources of information (e.g., insurance claims data). The data is automatically and continuously extracted and reformatted to specifically focus the attention of the healthcare provider on the needed care of his/her patient population or panel sharing a single condition according to evidence-based &/or nationally recognized guidelines. Thus, patients in need of specific care are automatically identified irrespective of their own compliance with their healthcare provider's request.

Healthcare providers are motivated to act upon the above information through exposure to automated feedback on their healthcare performance results for their patient population with a similar condition. Further motivation may occur as their performance is compared to the top performers in their peer group. Analysis of data shows that this process of benchmarking is key to engaging healthcare providers' attention toward improving care related to a specific condition. Furthermore, the data used to calculate this benchmarking feedback can be extracted from the same data sources as previously utilized for patient tracking.

To further support healthcare improvement, providers have access to national and other condition-related guidelines, published evidence and review papers, as well as provider and patient-directed resources within the invention. This is particularly powerful as the links to medical information are embedded in the same system and are pertinent to the same medical condition related to individual and patient populations.

In summary, the invention will accomplish the following:
(1) Patient tracking and identification of patient care deficiencies, to include:
  Identification of populations of patients with the a similar condition Alerts of overdue care necessary to monitor status of condition (e.g., blood pressure monitoring for hypertension)

Alerts identifying patient candidates for screening and/or preventive tests or measures Alerts of overdue laboratories to monitor medication safety (e.g., PT/INR testing on patients receiving warfarin to determine appropriate dose changes)

Stratification of patients based on risk of a negative healthcare outcomes (e.g., ordering patients by highest risk for heart attack).

(2) Benchmarking of healthcare provider performance with automated feedback and (3) Timely provision of relevant medical evidence and guidelines. These three functions are provided automatically and continuously, using data extraction methodology from an EMR.

The forgoing summary is intended only as a summary of the various aspects of the disclosed embodiment of the invention and should not be construed as limiting the scope of the invention as set forth in the appended claims. Additionally, aspects and advantages of the invention will be apparent from the following description of a preferred embodiment illustrated by the accompanying drawings.

BRIEF DESCRIPTION OF THE DRAWINGS

FIG. 3 is an example of how patient charts are viewed in an EMR

FIG. 5 illustrates the aggregation of disease and condition specific data

FIG. 11 is a technical process diagram of the preferred embodiment.

DETAILED DESCRIPTION

The present invention is embodied in an apparatus and a method to identify and track key care elements of patient populations with specific health conditions. This invention is predicated on the use of an electronic medical record (EMR) (see FIG. 3) in which patient-specific data elements are stored in a retrievable manner. Required patient-specific data elements that would exist in an EMR include patient demographics, diagnoses, medications and laboratory data.

Figure 1:
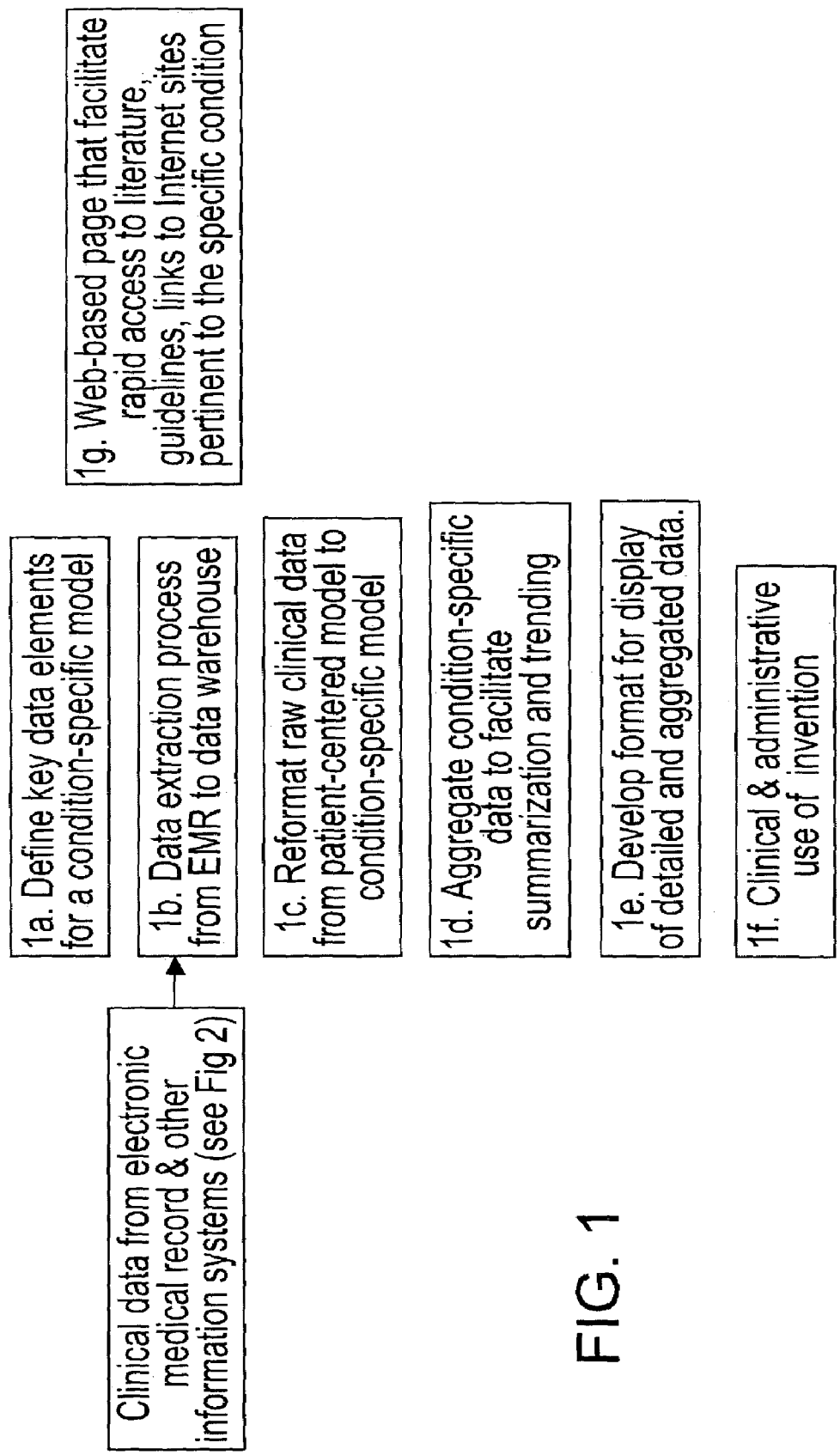
FIG. 1 is a flow-chart illustrating a preferred embodiment of the invention.

FIG. 1 is a high-level flowchart illustrating the overall process of a preferred embodiment of the present invention. Box 1a of FIG. 1 indicates the procedure for determining the data elements that are central to the healthcare outcomes of patients with a specific disease or condition. Many health conditions (e.g., diabetes, hypertension, heart disease) are associated with key data parameters that highlight opportunities for care process or outcome improvement. Examples of key data elements include whether a necessary test was rendered or not (e.g., cholesterol test, blood pressure measure, EKG), risk factors for a negative outcome, (e.g., high blood pressure, diabetes, old age, increased risk of heart attack), or results of condition-specific tests (e.g., cholesterol level, blood pressure level, drug level). During this data identification process the data necessary for monitoring outcomes and tracking of healthcare improvement opportunities are delineated.

Figure 2:
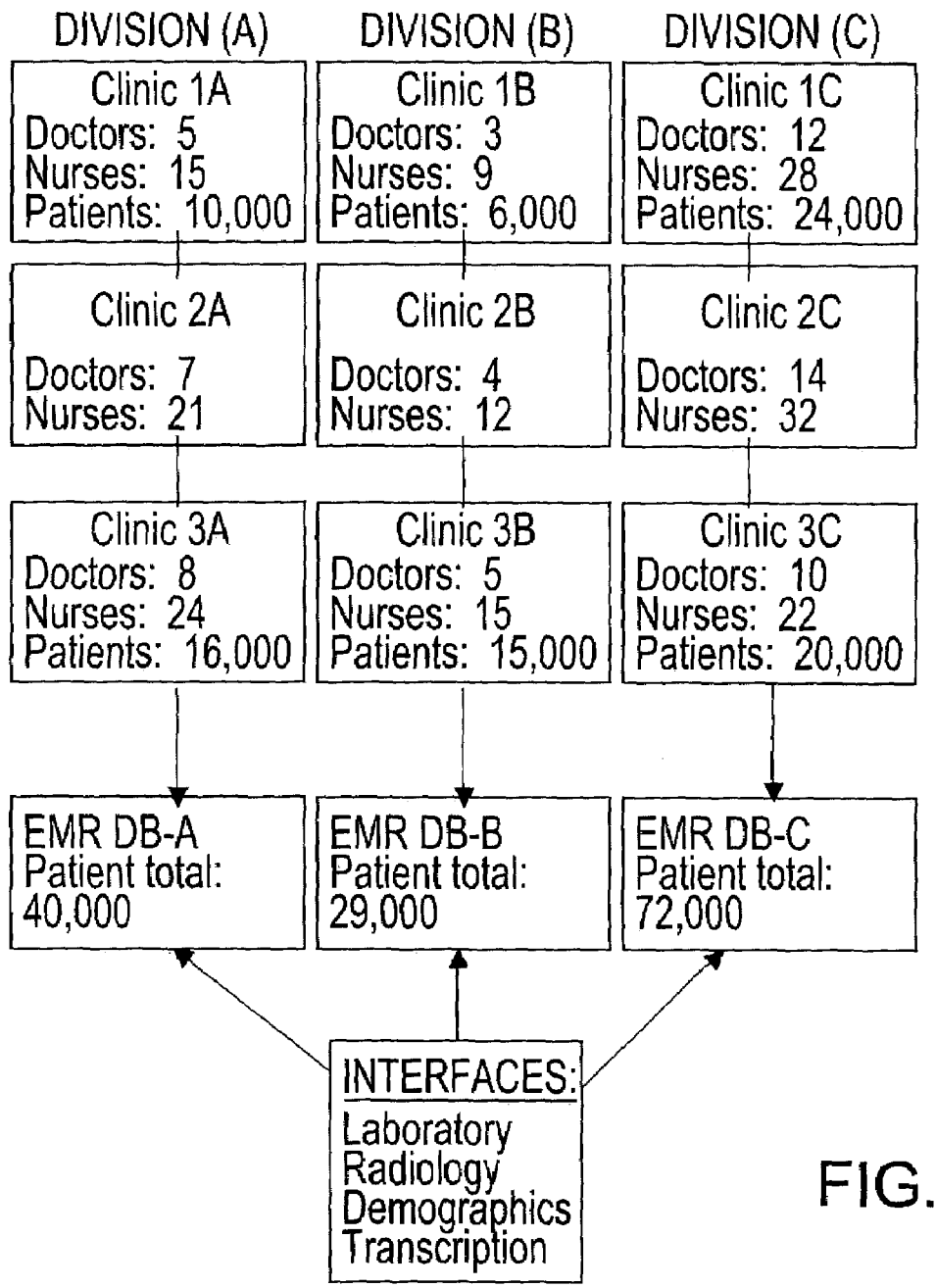
FIG. 2 illustrates multiple clinics data being stored in a single EMR database

Inherent in existing EMR systems is the storage of patient data in large database management systems (DBMS), such as Oracle. As illustrated in FIG. 2, the medical records of patients cared for by one or more healthcare providers in one or more clinics (Clinic 1A, 2A, 3A) can be stored in a single EMR database (EMR DB-A). This data has been entered into the EMR by a healthcare provider or staff in the normal process of documenting care, or is interfaced from other information systems (e.g., laboratory, radiology, transcription).

In the context of the present invention, the key data elements that were defined as described above are extracted from one or more EMR databases, as denoted in FIG. 1b. The data extraction process is fully automated and can be scheduled to occur as often as required (e.g., hourly, daily). The extracted data elements then populate the invention's data warehouse.

Existing EMRs present information in a format analogous to traditional paper charts, so that healthcare information can be viewed on only one patient at a time. This concept is further illustrated in FIG. 3. where each row represents one patient's data and that data can only be viewed one patient at a time. In this patient-centered model, healthcare providers are typically only prompted to view a patient's data when that patient initiates a phone call or office visit.

Figure 4:
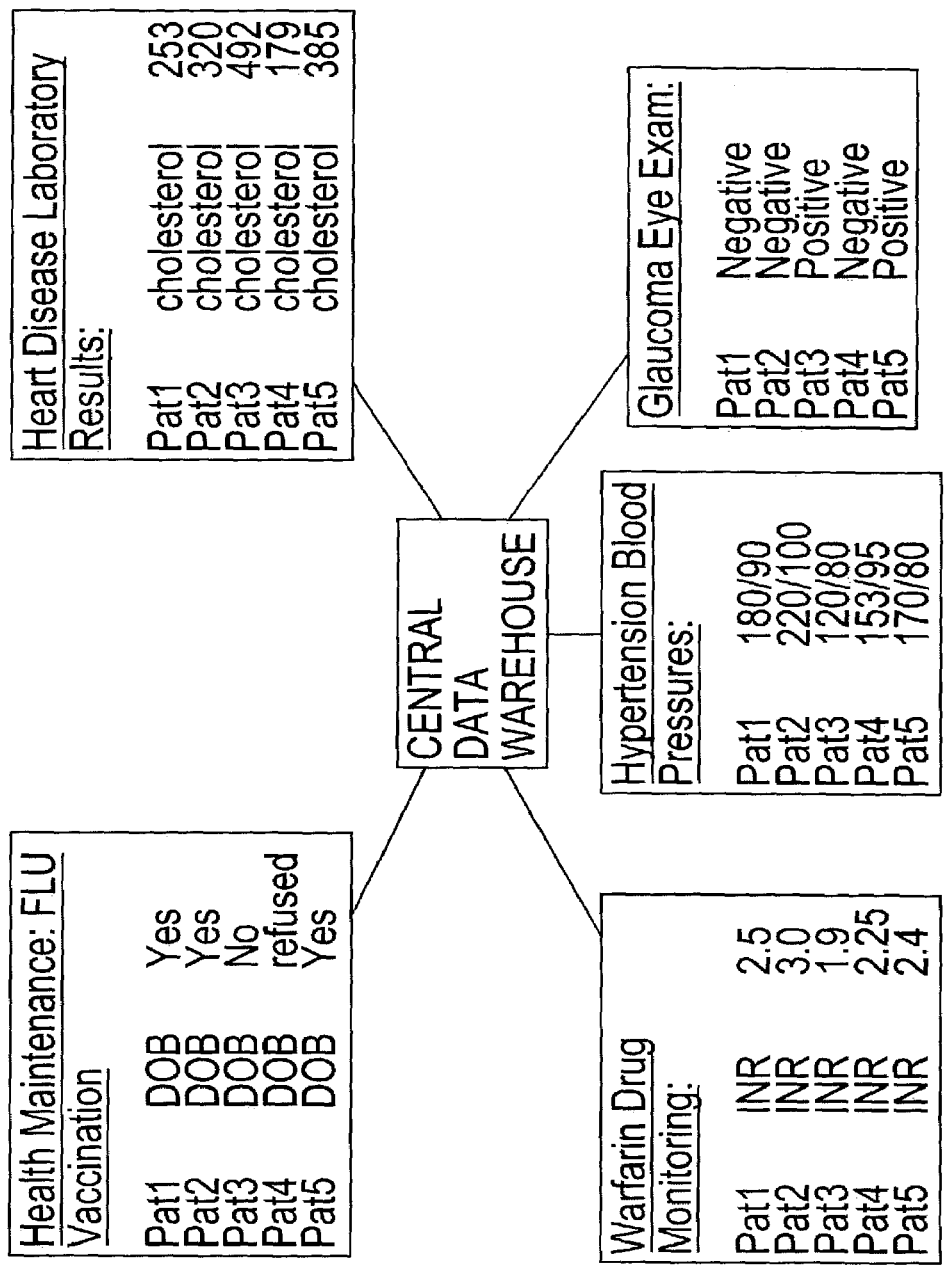
FIG. 4 illustrates patients information pertinent to a common disease state or condition are grouped.

FIG. 1c. denotes the process in which the invention reformats and presents data in the condition-specific model. The reformatting process groups key data elements for patients who share a common condition (see FIG. 4). For example, efficiency and quality of care can be improved when healthcare providers or staff can manage a list of patients with hypertension by viewing the date and value of the last blood pressure assessment. In doing so, patients overdue for a blood pressure check can be rapidly identified and contacted. Similarly, patients with an elevated blood pressure can be identified and treated.

Healthcare providers can be further aided in their management of patients by accessing aggregate information (see FIG. 1d.) that provides a richer picture of a patient's risks and benefits for health outcomes. For example, several risk factors can add up to increase a patient's risk of heart disease. Aggregate data can be used as decision support to weigh treatment options against an individual patient's risk. A patient's risk of having a heart attack in the next 10 years can be calculated based on the presence or absence of the following risk factors: hypertension, diabetes, cholesterol level, age, gender, family history, and personal history of previous heart disease. Knowing a patient's specific 10-year risk will guide discussions with patients and treatment decisions regarding risk factors such as cholesterol (FIG. 5). High-risk patients identified in a condition-specific model that includes risk calculation can be contacted and offered beneficial care even when they have not initiated an encounter.

FIG. 1d. also denotes the capability for summary views of aggregate data. A healthcare healthcare provider can assess and potentially improve the care he/she is providing by monitoring their quality of care in all their patients with a specific condition. This invention not only allows for aggregation of data on individual patients as described above, but also facilitates the aggregation of data in the warehouse for a population of patients with the same disease or condition. In keeping with the heart disease risk example from above, a healthcare provider can view data on the overall percentage of their high-risk patients who have achieved their cholesterol goals. The ability to present the healthcare provider with multiple summary parameters that have been recommended by available medical evidence or national standards enables that healthcare provider to monitor and trend the quality of care they provide. To further assist healthcare providers in evaluating and monitoring their care, this invention calculates a benchmark for comparison. The benchmark is usually calculated from top performing healthcare providers in the data warehouse for each specific care parameter (e.g., cholesterol goal attainment).

In addition to aggregating warehouse data on individual patients and populations of patients, this invention aggregates data for multiple healthcare providers. In doing so, the overall performance of a grouping of healthcare providers in a clinic or health system can also be assessed, monitored and trended.

FIG. 1e. represents the process of displaying individual and aggregated data from the warehouse on the personal computer of the healthcare provider or administrator for use. Periodically, a scheduled process is initiated to move data, using customized Sequential Query Language, from the back-end database of the EMR to populate the data warehouse. The preferred embodiment described herein utilizes a query frequency of twenty-four hours. The invention does allow for more frequent querying, up to real-time. Based on the identification of the user, the invention accesses the individual and aggregated data that is related to that user in the warehouse.

When providers initiate access to the invention via a standard web browser, the invention validates the privileges of the healthcare provider and passes a Hypertext Transport Protocol (HTTP) request to the web server. The web server, upon receiving the HTTP request, creates an instance of the invention's business objects. The business objects access the data warehouse and retrieve the requested information. The information is formatted into a graphic representation using an industry-standard graphing application. Using Remote Data Services (RDS), the business objects transfer a disconnected client-side record set to the web server. In parallel, the graphic representations are also sent to the web server. The web server then assembles the user interface from the RDS set and graphs. This data is formatted into HyperText Markup Language (HTML) and forwarded to the web browser as a HTTP response.

As additional operations such as navigation, sorting, or printing are performed on the data set, the RDS proxy enables client-side activity without requiring additional direct access to the data warehouse.

Figure 6:
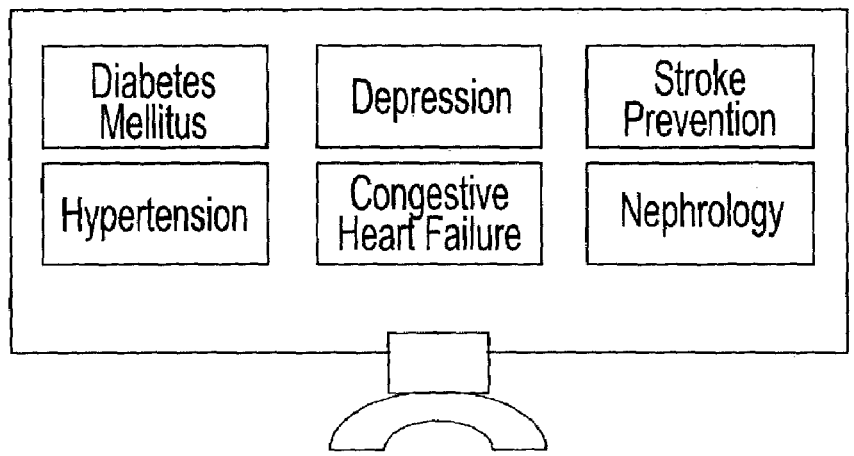
FIG. 6 is a diagram illustrating an example of the inventions main menu
Figure 7:
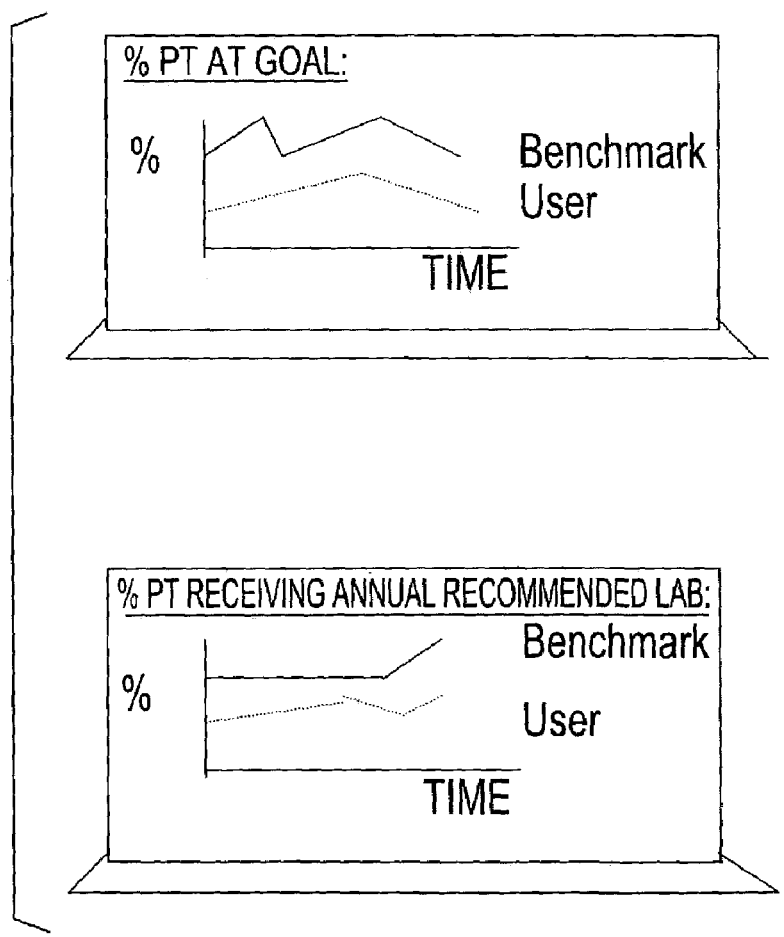
FIG. 7 illustrates "benchmarking" in the invention
Figure 9:
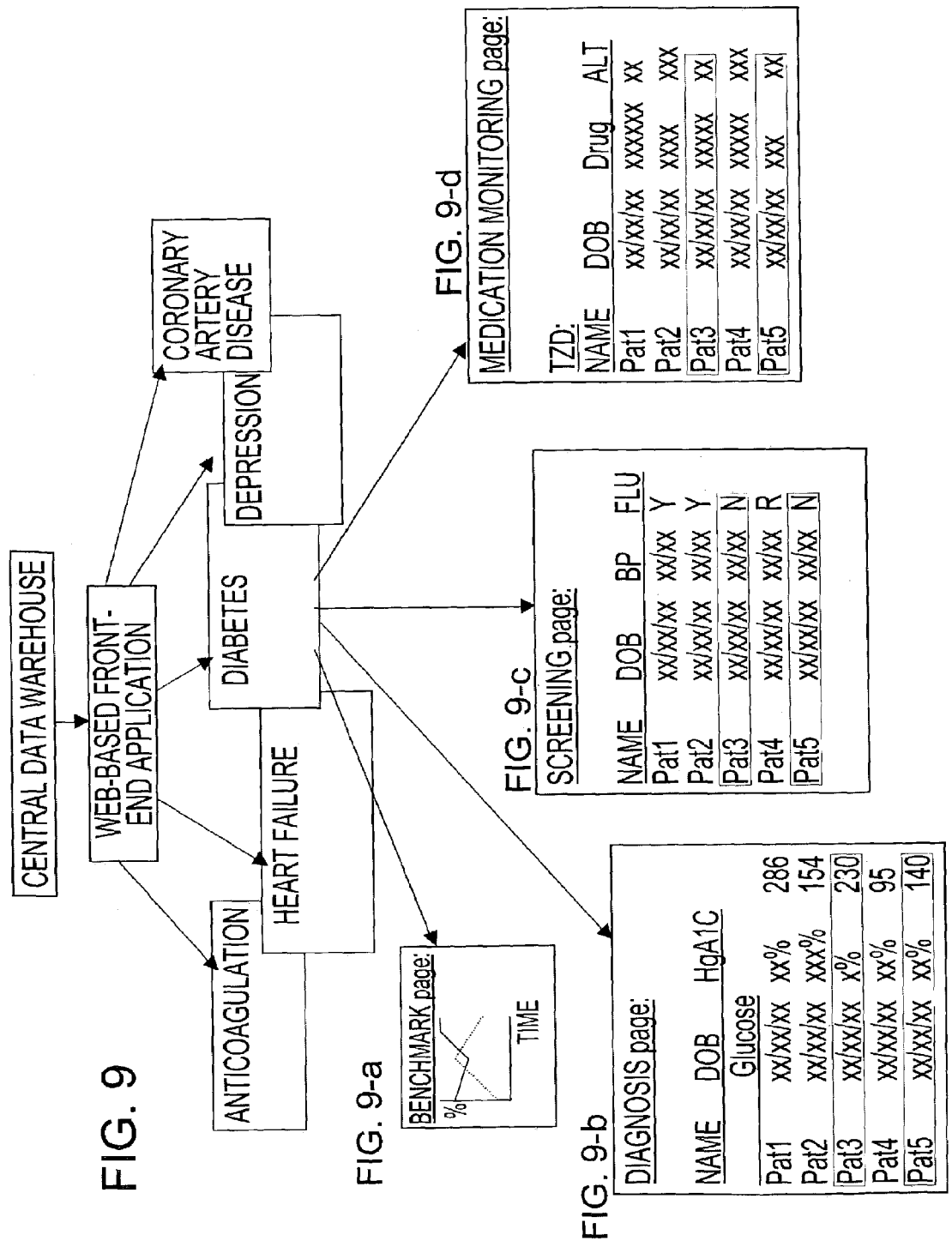
FIGS. 9a-d illustrates the formatting for display of detailed and aggregated data
Figure 10:
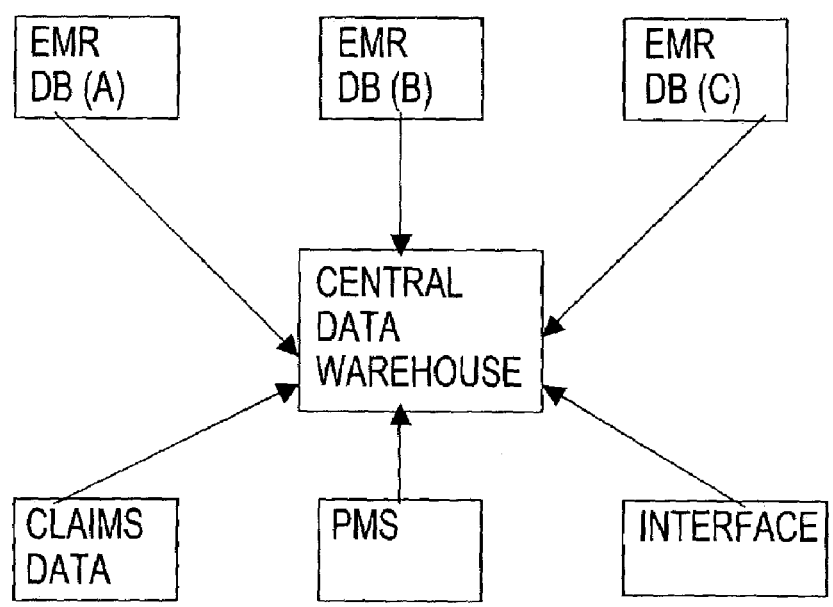
FIG. 10 illustrates import of data from multiple sources to the central data warehouse

Having described the process of collecting the data, the use of that data is described as follows:

The first display or web-based page is the main menu that allows the user to select which disease or condition they would like to view (FIG. 6). Options of available disease or condition-specific modules are governed by user-assigned privileges. Once a disease or condition-specific module is selected, the user opens to the default page that displays his/her patient-specific performance on parameters central to that disease or condition as compared to the appropriate benchmark (FIG. 7, FIG. 9-a). Users move from page to page by selecting among descriptive electronic tabs. Standard tabs across disease or condition-specific tracking systems include the performance & benchmark page, resource page, and help page. The existence or formatting of additional pages is guided by the needs of each individual disease or condition.

Figure 8:
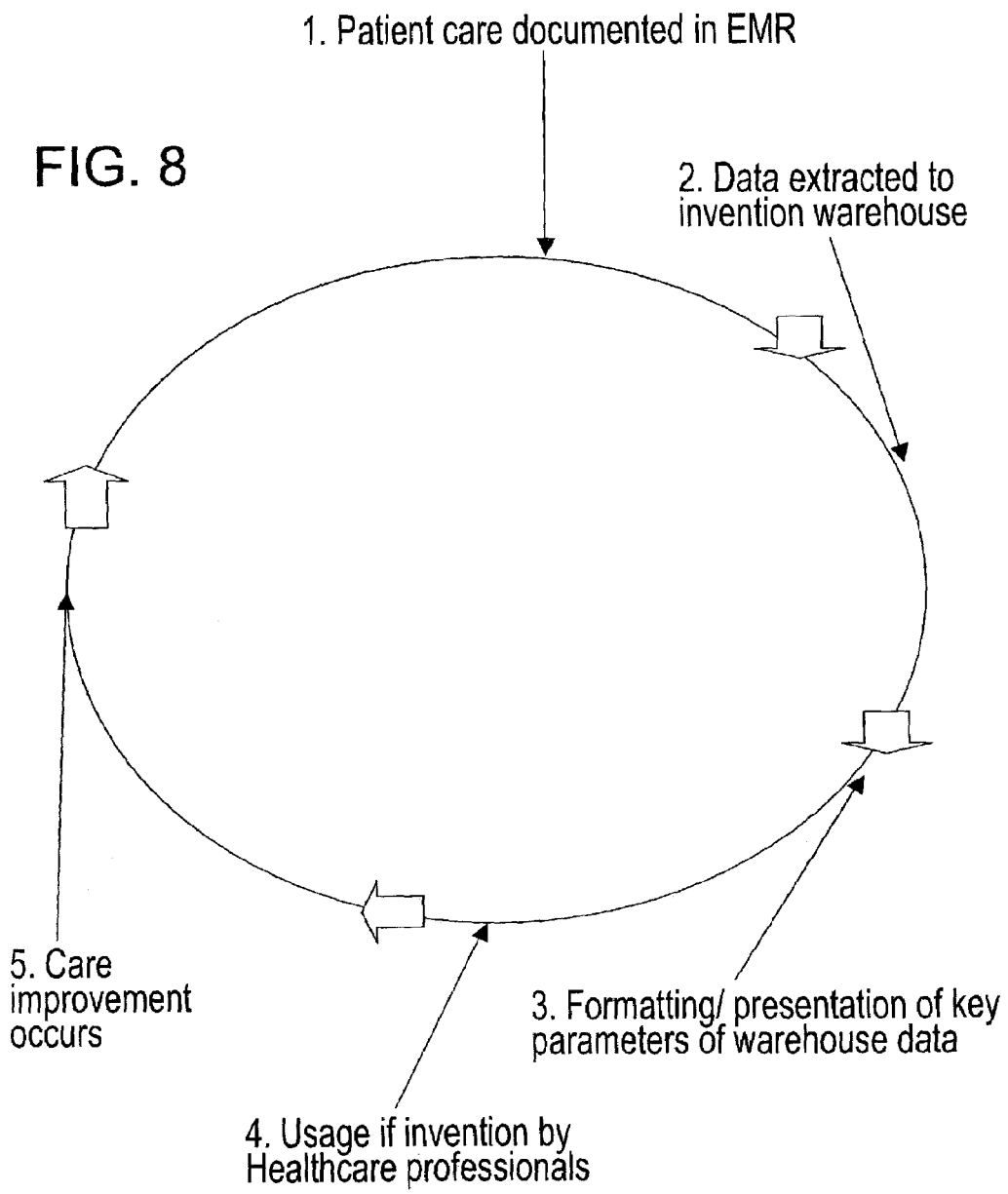
FIG. 8 illustrates the continuous cycle of data between the EMR and the invention

Whereas the performance & benchmark page allows the healthcare provider to monitor population parameters, it is the subsequent pages that allow the healthcare provider to identify specific patients and care opportunities. Using this invention, the healthcare provider can address these specific care opportunities to provide the needed care. (FIG. 1-f) All care (e.g., office visit, laboratory ordered, vital signs assessed, medication prescribed) is documented in the electronic medical record. The invention then continually updates the warehouse with this new information allowing care improvements to be rapidly reflected on the performance & benchmark page (FIG. 8).

The subsequent pages provide patient-specific information presented in such a way to facilitate medical decision-making. The content and therefore format of each page is driven by the medical needs of that disease or condition. For example, because hypertension is a disease that is vastly under-diagnosed, a page is devoted to displaying patients who have elevated blood pressures, but have not been diagnosed in the electronic medical record with that condition (FIG. 9-b). The diagnosis page is created by accessing data on the user's patients without evidence of a diagnosis of hypertension in the warehouse. The blood pressures of each of these patients are then evaluated among warehouse data. Each patient with an elevated blood pressure is presented on the page. By selecting this page, a healthcare provider is able to quickly view all his or her patients who are likely to have undiagnosed hypertension. The healthcare provider may decide to add the diagnosis to the patient's chart and/or prompt and office visit for further assessment.

Another subsequent page is devoted to monitoring treatment parameters. For example, published guidelines and medical evidence support the annual measurement and monitoring of several parameters in the care of patients with diabetes (e.g., HgbA1c, LDL cholesterol, blood pressure, and prescription of a daily aspirin). To facilitate this care, the diabetes module of the tracking system accesses all the user's patients with a diagnosis code signifying diabetes. The data parameters to monitor care for these patients are extracted from the warehouse and displayed. When the user accesses the invention and selects this page, he/she is presented with the list of all his/her patients with diabetes and the status of each of the pertinent care parameters (FIG. 9-c). Based on this information, the healthcare provider may order a test that is overdue, or determine that further treatment is necessary to achieve a patient's diabetic goals (e.g., prescribe a cholesterol-lowering medication to achieve the recommended LDL-cholesterol). In the case where a medical decision is facilitated by evaluating a key parameter over time, the invention provides the user with the ability to drill down to see parameter history. An example might be hypertension, in which the healthcare provider may want to view all blood pressures taken in the last six months to determine if a medication change is warranted.

Similarly, the invention allows for the tracking of parameters key to monitoring safe medication use.(FIG. 9-d) For example, some medications can cause side effects such as liver disease. To prevent a drug-induced case of liver disease, enzymes can be monitored by laboratory tests that will signal liver damage before the problem becomes irreversible. In cases such as this, the invention will identify patients taking this high-risk medication and extract the date of procurement and results of the recommended laboratory tests. A user viewing this page can quickly determine if a laboratory test is overdue or if the last result indicates possible liver damage.

Beyond monitoring for safe drug use, the invention can also identify cases of potentially harmful drug-drug or drug-disease interactions. For example, a drug-drug interaction between the anticoagulant warfarin (Coumadin®) and the antibiotic Septra® can cause hemorrhage. This invention would reveal the patients with evidence of active prescriptions for these two medications, alerting the healthcare provider to a potentially dangerous drug interaction. An example of a drug-disease interaction is the interaction of anti-inflammatory agents (e.g., ibuprofen, naproxen, Vioxx®) and the disease, heart failure. When an anti-inflammatory agent is prescribed to a patient with heart failure, that patient is put at increased risk of kidney failure. This invention would identify all of a user's patients with heart failure and reveal whether any of these patients also had an active prescription for an anti-inflammatory agent. Thus, dangerous interactions between medical conditions and medications can be identified and resolved.

The "resource" page provides the user with access to electronic information and tools to assist them in the care of their patients with that disease or condition (FIG. 1-g). Examples of materials that can be accessed from the resource page include guidelines, published review articles and clinical trials, patient educational materials, and links to relevant Internet sites. The user accesses the selected document (usually in a PDF format) from their location on a network. The availability of this aspect of the invention allows the healthcare provider to improve the quality of care provided. Documents on the resource page can be used to improve medical decision-making by providing quick access to the latest published studies and guidelines. Similarly, the resource page can be used to improve patient understanding and compliance by providing quick access to printable educational materials and links geared toward patients.

The "help" page allows the user to access documentation to assist in navigating the invention. Included in the help page is an overview of how the invention can be used to improve patient care, as well as systems of care. Additionally, the technical aspects of how to use the invention, along with definitions of key words and search strategies are included in the help page. The help page includes an email link to facilitate communication between the end-user and a product administrator.

Usage Reporting—The invention includes a mechanism for tracking of users' activity within the invention. Each time the invention is accessed the occurrence is recorded and tracked. Administrative reports detail the date and pages viewed by user. These reports, which can be updated real time (e.g., hourly, daily), are accessed within the invention by users granted administrative privileges.

Alerts & Interventions—Alerts are available in the invention when a patient is at immediate risk signified by a parameter that is out of safe range or a high-risk drug interaction. The user selects the threshold that will trigger the alert and the method of alert delivery. For example, a blood test called INR is used to monitor the anticoagulant, warfarin. The recommended INR range for most patients is between 2.0 and 3.5. As the INR falls below 2.0, patients are at increased risk of clots and strokes. As the INR increases above 5.0, patients are at increased risk of hemorrhage. The user can indicate the lower and upper INR result that would trigger the alert. The delivery of the alert is also selected by the user and may include a message in the invention, or in email, the EMR, or by pager or cell phone.

In the case where care is needed, but the patient is not at an immediate risk, care can be facilitated by the invention. Examples of interventions include a letter template requesting that patient(s) return for an overdue visit or test. All patients identified meeting the definition of overdue could be selected for an automated production of the letter and mailing envelope. Alternatively, once triggered by the user, the invention could send an email to patients requesting their return for an overdue visit or test or to alert them to the availability of a newly available therapy.

In brief summary, the invention enables a health care provider to more efficiently and effectively treat his/her patient population as particularly relates to chronic health conditions. The invention presumes the existence of essential data available from a source of recorded patient date, i.e., a patient data record such as the known electronic medical records (EMR) that are commonly accumulated for patient populations of health care providers. The invention is then the definition of goals (e.g., improved care for at-risk heart patients) and the identification of data that will enable the provider to electronically identify existing or threatened medical conditions of patients within his care and/or monitor the progress of these patients in comparison with designated benchmarks established for that condition. Numerous other advantages and uses have been identified and will become apparent to others from the descriptions provided herein. Accordingly, the invention is not limited to the examples and descriptions as provided above, but rather encompasses the full scope of the claims appended hereto. It is to be further understood that the term health care providers encompasses doctors, nurses, assistants, administrators and others who utilize the invention for the benefit of patients identified as having such existing or threatened chronic health condition. Further, the term patient outcomes encompasses all of the results and effects of health-care processes. The term includes intermediate results of care, such as blood pressure or cholesterol level. Intermediate outcomes reliably predict longer term health outcomes.

The invention claimed is:

1. A process for enhancing the health care of patients which comprises:

receiving a selection of an existing or threatened health related condition;

automatically extracting patient information electronically from an existing electronic medical record database, the electronic medical record database containing patient-specific data elements stored in a retrievable manner, where the data is entered in routine patient care documentation by healthcare providers, by staff, or through interfaces with other information systems;

querying extracted patient information based on criteria, wherein the criteria correlate to the selected existing or threatened health related condition;

identifying a population of patients having the selected existing or threatened heath related condition in common based on the query;

retrieving selected information from the extracted patient information for said identified population of patients to assist a health care provider in treatment of said identified patients;

determining, in a computer having a processor, values of a group of standardized and/or published medical treatment guidelines, the values appropriate for the selected condition or disease;

formatting the retrieved information to enable analysis of the selected existing or threatened health care condition of said identified population of patients, said formatting including identifying patient-specific data elements for the identified population of patients that fall outside the determined values of the standardized and/or published medical treatment guidelines for the selected condition or disease;

providing electronic accessibility of the formatted information to the health care provider to enable said health care provider to utilize the formatted information to improve patient outcome, said providing including displaying the identified patient-specific data elements for the identified population of patients, the data elements concurrently displayed for the identified patients in an aggregate view; and generating alerts for patients within said population of patients, said alerts including at least each of the following alerts:
- a first alert identifying overdue care to monitor status of data elements of the selected existing or threatened health related condition of the population of patients,
- a second alert identifying patient candidates for screening and/or preventative tests, and
- a third alert of overdue lab tests to monitor medication safety.

2. A process as defined in claim 1 which further comprises at least daily repetitive querying of said electronic medical record for updating the information; and
stratifying the population of patients based on risk of a negative healthcare outcome.

3. A process as defined in claim 2 which further comprises said formatting and said information enabling analysis of patients' progress resulting from treatment provided by said health care provider.

4. A process as defined in claim 3 which further comprises enabling comparison of treatments and progress of patients.

5. A process as defined in claim 4 which further comprises enabling comparisons of patient outcomes of different health care providers, where feedback is generated for a selected healthcare provider comparing patient outcomes for patients of the selected healthcare provider to patient outcomes of top performing healthcare providers, where the patient outcomes are compared for patients with the selected existing or threatened health related condition in common.

6. A process as defined in claim 1 which further comprises providing updated reference materials related to said health care condition and enabling the provider access to said reference materials.

7. A process as defined in claim 5 which further comprises applying benchmarking methodology to said formatted information.

8. A process as defined in claim 1 wherein information is initially recorded in an electronic medical record and which further includes transferring selected information from said electronic medical record to a data warehouse where the information is formatted as defined in claim 1.

* * * * *